US009840723B2

(12) United States Patent
Pedersen

(10) Patent No.: US 9,840,723 B2
(45) Date of Patent: Dec. 12, 2017

(54) PROCESS FOR SIMULTANEOUS SACCHARFICATION AND FERMENTATION OF WHEY PERMEATE

(71) Applicant: NOVOZYMES A/S, Bagsvaerd (DK)

(72) Inventor: Sven Pedersen, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/890,078

(22) PCT Filed: May 13, 2014

(86) PCT No.: PCT/EP2014/059756
§ 371 (c)(1),
(2) Date: Nov. 9, 2015

(87) PCT Pub. No.: WO2014/184189
PCT Pub. Date: Nov. 20, 2014

(65) Prior Publication Data
US 2016/0108440 A1     Apr. 21, 2016

(30) Foreign Application Priority Data
May 14, 2013   (EP) .................................... 13167667

(51) Int. Cl.
| | | |
|---|---|---|
| C12P 7/06 | (2006.01) | |
| C12P 7/14 | (2006.01) | |
| C12N 9/38 | (2006.01) | |
| C12N 1/00 | (2006.01) | |
| C07H 21/04 | (2006.01) | |
| C12P 7/08 | (2006.01) | |

(52) U.S. Cl.
CPC .. *C12P 7/14* (2013.01); *C12P 7/08* (2013.01)

(58) Field of Classification Search
None
See application file for complete search history.

(56) References Cited

PUBLICATIONS

Zarate et al. Oligosaccharide Formation During Enzymatic Lactose Hydrolysis: A Literature Review, Journal of Food Protection. vol. 53, No. 3. pp. 262-268 (Mar. 1990).*
Domingues et al. (Construction of a flocculent Saccharomyces cerevisiae strain secreting high levels of Aspergillus niger β-galactosidase, Appl Microbiol Biotechnol (2002) 58:645-650).*
Prenosil et al. Biotechnology and Bioengineering, vol. 30, pp. 1026-1031 (1987).*
Passerat et al. Lactase activity of Bifidobacterium bifidum, Nutrition Research, vol. 15, Issue 9, Sep. 1995, pp. 1287-1295.*
Domingues et al, 2001, Biotechnol Bioengg 72(5), 507-514.
Gawel et al, 1978, J Food Sci 43 (3), 1031-1032.
Gibbons et al, 1983, Biotechnol Bioengg 25 (9), 2127-2148.
Goulas et al, 2007, Appl Microbiol Biotechnol 76 (7), 1365-1372.
Grosova et al, 2009, Food Chem 116 (1), 96-100.
Guimaraes et al, 2008, Bitoechnol Lett 30, 1953-1958.
Hagerdal et al, 1985, Biotechnol Bioengg 27(6), 914-916.
Mehaia et al, 1990, Bioprocess Engg 5, 57-61.

* cited by examiner

*Primary Examiner* — Iqbal H Chowdhury
(74) *Attorney, Agent, or Firm* — David Fazzolare

(57) ABSTRACT

A process for producing ethanol from lactose containing substrates, comprising simultaneously saccharifying the substrate to produce monosaccharide and fermenting the monosaccharide to produce ethanol at a pH from 3.5-5.5, using a fermenting organism, wherein saccharification is carried out in the presence of a lactase, and wherein the fermenting organism is a *Saccharomyces* sp., and the ratio between the incubation time required for obtaining at least 90% hydrolysis of the lactose present in the substrate ($t_{-1}$) and the total fermentation time ($t_2$) is in the range of 0.1 to 1, and the *Saccharomyces* sp. is added in amounts that will result in an ethanol yield of at least 70% w/w of the theoretical ethanol yield from lactose by the end of fermentation.

24 Claims, 5 Drawing Sheets

SEQUENCE LISTING

<160> NUMBER OF SEQ ID NOS: 2

<210> SEQ ID NO 1
<211> LENGTH: 3996
<212> TYPE: DNA
<213> ORGANISM: Bifidobacterium bifidum

<400> SEQUENCE: 1
atgaagaaac cgttggggaa aattgtcgca agcaccgcac tactcatttc tgttgctttt    60
agttcatcga tcgcatcggc tgttgaggac gccacgagaa gtgatagcac cactcaaatg   120
tcatccacac cggaagtagt gtattcttca gcagtcgatt ccaaacagaa tagaacatct   180

```
gactttgatg ccaattggaa attcatgctt tcggatagcg tacaggcgca ggatccggca    240
tttgatgatt ctgcgtggca gcaggttgat ctgcctcatg actatagcat tacacagaaa    300
tacagccagt ctaatgaagc ggaatcggcg tacttacctg ggggaacagg atggtataga    360
aaatctttca caattgacag ggacttagcg ggtaagcgga tcgcgatcaa ctttgatgga    420
gtctatatga atgcgactgt gtggttcaat ggcgtgaagt tggggacaca cccatatggg    480 tattcccct tttcatttga cctcactggg aacgcgaagt ttgggggaga gaataccatt    540
gttgtgaaag tcgaaaacag attgccgtca tcccgctggt actctggttc aggcatttac    600
cgcgatgtaa ctttaaccgt gacggacgga gtccatgttg gaacaatgg tgttgctatc    660 aaaacaccaa gcttggcaac tcagaatgga ggcaatgtga ctatgaacct cacaacaaaa    720
gtggccaacg acacaaaagc agcagccaat atcacactta acaaaccgt gtttccgaag    780 ggaggcaaga cggacgctgc aataggaaca gtcacgacgg catctaagtc cattgcagca    840
ggagcgtccg cagatgtgac atcaacaatt acggcagcgt cacctaaact gtggtcgata    900
aagaatccga atttgtacac agtgcgcacc gaggtgttaa acggaggtaa agttttggac    960
acgtatgata cagaatatgg gtttcgctgg actggatttg atgcaacatc aggattcagc    1020
ttaaacggag agaaggttaa acttaaagga gtgtcaatgc atcacgatca gggttctttg    1080
ggagcggttg cgaatcggag agccatcgaa cgacaggtcg aaatcttaca gaaaatggga    1140
gtcaattcaa tccggacgac acacaatccg gcagcaaaag ccttgattga cgtatgtaac    1200 gaaaaggag tattagtggt tgaagaagtc tttgacatgt ggaaccgctc caagaatgga    1260
aatacagaag actatggaaa gtggtttggt caagccatag caggggataa cgctgtcttg    1320
ggtggagata aggacgaaac gtgggcgaag tttgacttaa catcaacaat caatcgcgat    1380
cgcaacgctc cgagtgtgat aatgtggtcg cttggcaacg agatgatgga aggtattagc    1440
ggatctgtat cggggtttcc ggctacttcc gcaaaactcg tggcatggac aaaagcggct    1500
gattccactc gacctatgac ttatggagac aacaagatca aagctaactg gaatgagtcg    1560
aatacgatgg gagacaactt aacggcaaat gggggagtcg tcggaacgaa ctattccgat    1620
ggcgctaact atgacaaaat ccggacaact catccctctt gggcgatcta tggctctgaa    1680
acagccagtg ctatcaacag caggggaatc tataacagaa caactggcgg agcccaaagc    1740
tccgacaaac agcttacgtc atacgacaac agcgcagttg gctggggtgc agtagcctca    1800
agcgcctggt atgatgtggt ccagcgcgac tttgttgcag gaacttatgt gtggactggt    1860
tttgactact taggcgaacc gacgccttgg aacggtactg gctcaggcgc tgtcggctca    1920
tggccgtccc cgaaaaactc ttactttggg attgtggata cagcaggctt tccgaaagac    1980
acgtactact tttaccaatc tcaatggaac gatgatgtcc atacgcttca tatcttacct    2040
gcgtggaacg aaaatgtcgt ggcgaaaggc tccggcaaca atgtgccggt tgtagtgtat    2100
acagatgcgg ctaaagtaaa actgtacttt actcctaagg gctcgacgga aaaacgattg    2160
atcgggagga aagtttcac gaagaaaacc acagccgctg gctacacgta ccaggtgtac    2220
gagggagcgg acaaagatag cacggctcac aaaaacatgt atctgacttg gaatgttccg    2280
tgggcagaag gacgatatc agccgaagca tacgatgaga caaccgctt aatccccgaa    2340 ggcagcacgg aagggaatgc ctctgttaca acgacaggca agcagcaaa gttgaaggcg    2400 gatgcagatc ggaaaacgat taccgcagat ggcaaggatc tttcctatat cgaggtggac    2460
gtcacagatg ccaatggaca tatcgtgccg gatgcagcga atcgtgttac atttgacgta    2520
aaaggggcag gcaaactggt tggggttgac aacgggtcgt caccggacca tgatagttat    2580
```

```
caggctgaca ataggaaagc gtttagcggc aaagttttag ccatcgtgca gtcaactaaa   2640
gaagccggag aaatcacagt cacagcaaaa gctgacggat tacaatcttc gacggtcaag   2700
attgctacaa ctgcggttcc gggtacatca acggaaaaga cggttaggtc cttctactat   2760
agtagaaact actatgtgaa aactggcaac aaacctatcc tgccaagtga tgtggaggtt   2820
agatattcag acggcacatc cgatcgtcaa aacgtcacgt gggatgctgt ttcagatgat   2880
caaatcgcga aggctggctc tttttcagta gcgggaacag tggctggaca gaaaatctca   2940
gtccgtgtaa ctatgattga cgagattggg gcactgttga actattcagc ttcaacaccg   3000
gtaggaacac cagctgtttt gccaggctca aggccagcgg tactcccaga cggcacggtt   3060
acatctgcaa actttgctgt agattggacg aaacctgccg acaccgtgta caatacagct   3120
gggactgtga agtgcctgg acagcgaca gtctttggaa aagagttcaa agtcacagcg   3180
acaatcagag tacagagatc gcaggtcacg atcggaagtt ccgtctcagg taatgcactg   3240
agacttacgc aaaacattcc ggctgacaaa cagagtgata cacttgatgc aatcaaagac   3300
ggaagcacaa cagttgatgc aaacacgggt ggaggggcta atccgtccgc gtggacgaac   3360
tgggcttaca gcaaagcagg acacaatact gcagaaatca cgtttgagta tgcaacagag   3420
caacagctgg gccaaattgt aatgtacttc tttagagatt caaatgcggt acggtttccc   3480
gatgctggta aaaccaaaat ccagatatcg gcagatggca agaattggac agaccttgcg   3540
gcaacggaaa cgattgccgc tcaggagagt agtgaacgcg ttaaaccttt tacatacgac   3600
tttgcaccgg ttggcgcaac ctttgtgaaa gttacggtga cgaacgccga tacaacaacg   3660
ccgtcaggcg tagtttgtgc aggattaaca gaaatagagt taaagacggc aacaagcaag   3720
ttcgtcacaa acacttctgc ggcattatct tcgctgacgg ttaacgggac caaagtctca   3780
gacagcgtgc ttgcagctgg atcatacaac actcctgcca ttatcgcgga tgtaaaagcg   3840
gaaggcgaag gtaatgcgtc tgtcactgtg ttgcctgctc acgataacgt catccgtgtg   3900
attacagagt ccgaagacca tgttacaaga aaaacgtttta ccattaactt ggggacagaa   3960
caagaatttc ctgccgattc agatgaaaga gattaa                              3996
```

<210> SEQ ID NO 2
<211> LENGTH: 1331
<212> TYPE: PRT
<213> ORGANISM: Bifidobacterium bifidum

<400> SEQUENCE: 2

```
Met Lys Lys Pro Leu Gly Lys Ile Val Ala Ser Thr Ala Leu Leu Ile
1               5                   10                  15

Ser Val Ala Phe Ser Ser Ile Ala Ser Ala Val Glu Asp Ala Thr
            20                  25                  30

Arg Ser Asp Ser Thr Thr Gln Met Ser Ser Thr Pro Glu Val Val Tyr
        35                  40                  45

Ser Ser Ala Val Asp Ser Lys Gln Asn Arg Thr Ser Asp Phe Asp Ala
    50                  55                  60

Asn Trp Lys Phe Met Leu Ser Asp Ser Val Gln Ala Gln Asp Pro Ala
65                  70                  75                  80

Phe Asp Asp Ser Ala Trp Gln Gln Val Asp Leu Pro His Asp Tyr Ser
                85                  90                  95

Ile Thr Gln Lys Tyr Ser Gln Ser Asn Glu Ala Glu Ser Ala Tyr Leu
            100                 105                 110

Pro Gly Gly Thr Gly Trp Tyr Arg Lys Ser Phe Thr Ile Asp Arg Asp
```

```
            115                 120                 125
Leu Ala Gly Lys Arg Ile Ala Ile Asn Phe Asp Gly Val Tyr Met Asn
130                 135                 140
Ala Thr Val Trp Phe Asn Gly Val Lys Leu Gly Thr His Pro Tyr Gly
145                 150                 155                 160
Tyr Ser Pro Phe Ser Phe Asp Leu Thr Gly Asn Ala Lys Phe Gly Gly
                    165                 170                 175
Glu Asn Thr Ile Val Val Lys Val Glu Asn Arg Leu Pro Ser Ser Arg
                180                 185                 190
Trp Tyr Ser Gly Ser Gly Ile Tyr Arg Asp Val Thr Leu Thr Val Thr
            195                 200                 205
Asp Gly Val His Val Gly Asn Asn Gly Val Ala Ile Lys Thr Pro Ser
210                 215                 220
Leu Ala Thr Gln Asn Gly Gly Asn Val Thr Met Asn Leu Thr Thr Lys
225                 230                 235                 240
Val Ala Asn Asp Thr Lys Ala Ala Ala Asn Ile Thr Leu Lys Gln Thr
                245                 250                 255
Val Phe Pro Lys Gly Gly Lys Thr Asp Ala Ala Ile Gly Thr Val Thr
                260                 265                 270
Thr Ala Ser Lys Ser Ile Ala Ala Gly Ala Ser Ala Asp Val Thr Ser
            275                 280                 285
Thr Ile Thr Ala Ala Ser Pro Lys Leu Trp Ser Ile Lys Asn Pro Asn
290                 295                 300
Leu Tyr Thr Val Arg Thr Glu Val Leu Asn Gly Gly Lys Val Leu Asp
305                 310                 315                 320
Thr Tyr Asp Thr Glu Tyr Gly Phe Arg Trp Thr Gly Phe Asp Ala Thr
                325                 330                 335
Ser Gly Phe Ser Leu Asn Gly Glu Lys Val Lys Leu Lys Gly Val Ser
                340                 345                 350
Met His His Asp Gln Gly Ser Leu Gly Ala Val Ala Asn Arg Arg Ala
            355                 360                 365
Ile Glu Arg Gln Val Glu Ile Leu Gln Lys Met Gly Val Asn Ser Ile
370                 375                 380
Arg Thr Thr His Asn Pro Ala Ala Lys Ala Leu Ile Asp Val Cys Asn
385                 390                 395                 400
Glu Lys Gly Val Leu Val Val Glu Glu Val Phe Asp Met Trp Asn Arg
                405                 410                 415
Ser Lys Asn Gly Asn Thr Glu Asp Tyr Gly Lys Trp Phe Gly Gln Ala
                420                 425                 430
Ile Ala Gly Asp Asn Ala Val Leu Gly Gly Asp Lys Asp Glu Thr Trp
            435                 440                 445
Ala Lys Phe Asp Leu Thr Ser Thr Ile Asn Arg Asp Arg Asn Ala Pro
450                 455                 460
Ser Val Ile Met Trp Ser Leu Gly Asn Glu Met Met Glu Gly Ile Ser
465                 470                 475                 480
Gly Ser Val Ser Gly Phe Pro Ala Thr Ser Ala Lys Leu Val Ala Trp
                485                 490                 495
Thr Lys Ala Ala Asp Ser Thr Arg Pro Met Thr Tyr Gly Asp Asn Lys
                500                 505                 510
Ile Lys Ala Asn Trp Asn Glu Ser Asn Thr Met Gly Asp Asn Leu Thr
            515                 520                 525
Ala Asn Gly Gly Val Val Gly Thr Asn Tyr Ser Asp Gly Ala Asn Tyr
530                 535                 540
```

```
Asp Lys Ile Arg Thr Thr His Pro Ser Trp Ala Ile Tyr Gly Ser Glu
545                 550                 555                 560

Thr Ala Ser Ala Ile Asn Ser Arg Gly Ile Tyr Asn Arg Thr Thr Gly
                565                 570                 575

Gly Ala Gln Ser Ser Asp Lys Gln Leu Thr Ser Tyr Asp Asn Ser Ala
            580                 585                 590

Val Gly Trp Gly Ala Val Ala Ser Ser Ala Trp Tyr Asp Val Val Gln
        595                 600                 605

Arg Asp Phe Val Ala Gly Thr Tyr Val Trp Thr Gly Phe Asp Tyr Leu
610                 615                 620

Gly Glu Pro Thr Pro Trp Asn Gly Thr Gly Ser Gly Ala Val Gly Ser
625                 630                 635                 640

Trp Pro Ser Pro Lys Asn Ser Tyr Phe Gly Ile Val Asp Thr Ala Gly
                645                 650                 655

Phe Pro Lys Asp Thr Tyr Tyr Phe Tyr Gln Ser Gln Trp Asn Asp Asp
            660                 665                 670

Val His Thr Leu His Ile Leu Pro Ala Trp Asn Glu Asn Val Val Ala
        675                 680                 685

Lys Gly Ser Gly Asn Asn Val Pro Val Val Tyr Thr Asp Ala Ala
690                 695                 700

Lys Val Lys Leu Tyr Phe Thr Pro Lys Gly Ser Thr Glu Lys Arg Leu
705                 710                 715                 720

Ile Gly Glu Lys Ser Phe Thr Lys Lys Thr Thr Ala Ala Gly Tyr Thr
                725                 730                 735

Tyr Gln Val Tyr Glu Gly Ala Asp Lys Asp Ser Thr Ala His Lys Asn
            740                 745                 750

Met Tyr Leu Thr Trp Asn Val Pro Trp Ala Glu Gly Thr Ile Ser Ala
        755                 760                 765

Glu Ala Tyr Asp Glu Asn Asn Arg Leu Ile Pro Glu Gly Ser Thr Glu
770                 775                 780

Gly Asn Ala Ser Val Thr Thr Thr Gly Lys Ala Ala Lys Leu Lys Ala
785                 790                 795                 800

Asp Ala Asp Arg Lys Thr Ile Thr Ala Asp Gly Lys Asp Leu Ser Tyr
                805                 810                 815

Ile Glu Val Asp Val Thr Asp Ala Asn Gly His Ile Val Pro Asp Ala
            820                 825                 830

Ala Asn Arg Val Thr Phe Asp Val Lys Gly Ala Gly Lys Leu Val Gly
        835                 840                 845

Val Asp Asn Gly Ser Ser Pro Asp His Asp Ser Tyr Gln Ala Asp Asn
850                 855                 860

Arg Lys Ala Phe Ser Gly Lys Val Leu Ala Ile Val Gln Ser Thr Lys
865                 870                 875                 880

Glu Ala Gly Glu Ile Thr Val Thr Ala Lys Ala Asp Gly Leu Gln Ser
                885                 890                 895

Ser Thr Val Lys Ile Ala Thr Thr Ala Val Pro Gly Thr Ser Thr Glu
            900                 905                 910

Lys Thr Val Arg Ser Phe Tyr Tyr Ser Arg Asn Tyr Tyr Val Lys Thr
        915                 920                 925

Gly Asn Lys Pro Ile Leu Pro Ser Asp Val Glu Val Arg Tyr Ser Asp
930                 935                 940

Gly Thr Ser Asp Arg Gln Asn Val Thr Trp Asp Ala Val Ser Asp Asp
945                 950                 955                 960
```

-continued

Gln Ile Ala Lys Ala Gly Ser Phe Ser Val Ala Gly Thr Val Ala Gly
              965                 970                 975

Gln Lys Ile Ser Val Arg Val Thr Met Ile Asp Glu Ile Gly Ala Leu
              980                 985                 990

Leu Asn Tyr Ser Ala Ser Thr Pro Val Gly Thr Pro Ala Val Leu Pro
          995                 1000                1005

Gly Ser Arg Pro Ala Val Leu Pro Asp Gly Thr Val Thr Ser Ala
    1010                1015                1020

Asn Phe Ala Val Asp Trp Thr Lys Pro Ala Asp Thr Val Tyr Asn
    1025                1030                1035

Thr Ala Gly Thr Val Lys Val Pro Gly Thr Ala Thr Val Phe Gly
    1040                1045                1050

Lys Glu Phe Lys Val Thr Ala Thr Ile Arg Val Gln Arg Ser Gln
    1055                1060                1065

Val Thr Ile Gly Ser Ser Val Ser Gly Asn Ala Leu Arg Leu Thr
    1070                1075                1080

Gln Asn Ile Pro Ala Asp Lys Gln Ser Asp Thr Leu Asp Ala Ile
    1085                1090                1095

Lys Asp Gly Ser Thr Thr Val Asp Ala Asn Thr Gly Gly Gly Ala
    1100                1105                1110

Asn Pro Ser Ala Trp Thr Asn Trp Ala Tyr Ser Lys Ala Gly His
    1115                1120                1125

Asn Thr Ala Glu Ile Thr Phe Glu Tyr Ala Thr Glu Gln Gln Leu
    1130                1135                1140

Gly Gln Ile Val Met Tyr Phe Arg Asp Ser Asn Ala Val Arg
    1145                1150                1155

Phe Pro Asp Ala Gly Lys Thr Lys Ile Gln Ile Ser Ala Asp Gly
    1160                1165                1170

Lys Asn Trp Thr Asp Leu Ala Ala Thr Glu Thr Ile Ala Ala Gln
    1175                1180                1185

Glu Ser Ser Glu Arg Val Lys Pro Tyr Thr Tyr Asp Phe Ala Pro
    1190                1195                1200

Val Gly Ala Thr Phe Val Lys Val Thr Val Thr Asn Ala Asp Thr
    1205                1210                1215

Thr Thr Pro Ser Gly Val Val Cys Ala Gly Leu Thr Glu Ile Glu
    1220                1225                1230

Leu Lys Thr Ala Thr Ser Lys Phe Val Thr Asn Thr Ser Ala Ala
    1235                1240                1245

Leu Ser Ser Leu Thr Val Asn Gly Thr Lys Val Ser Asp Ser Val
    1250                1255                1260

Leu Ala Ala Gly Ser Tyr Asn Thr Pro Ala Ile Ile Ala Asp Val
    1265                1270                1275

Lys Ala Glu Gly Glu Gly Asn Ala Ser Val Thr Val Leu Pro Ala
    1280                1285                1290

His Asp Asn Val Ile Arg Val Ile Thr Glu Ser Glu Asp His Val
    1295                1300                1305

Thr Arg Lys Thr Phe Thr Ile Asn Leu Gly Thr Glu Gln Glu Phe
    1310                1315                1320

Pro Ala Asp Ser Asp Glu Arg Asp
    1325                1330

PROCESS FOR SIMULTANEOUS SACCHARFICATION AND FERMENTATION OF WHEY PERMEATE

CROSS-REFERENCE TO RELATED APPLICATIONS

This application is a 35 U.S.C. 371 national application of PCT/EP2014/059756 filed May 13, 2014, which claims priority or the benefit under 35 U.S.C. 119 of European application no. 13167667.8 filed May 14, 2013, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to a process for saccharification and fermentation of whey permeate to produce ethanol.

BACKGROUND OF THE INVENTION

Production of ethanol from cheese whey has traditionally been conducted using a yeast belonging to *Kluyveromyces* sp., e.g. *Kluyveromyces fragilis* or *Kluyveromyces marxianus*, since these fermenting organisms can directly ferment lactose to ethanol. However, these yeast suffer from the drawback that they are ethanol sensitive and therefore only processes applying low substrate concentrations and corresponding low ethanol yields have been feasible.

An alternative to using *Kluyveromyces* sp. as the fermenting organism is to use *Saccharomyces cerevisiae*. To make this possible the addition of enzymes, like e.g. a beta-galactosidase, is necessary in order to convert the lactose to fermentable sugars. Mehaia and Cheryan (Bioprocess Engineering 5 (1990), 57-61), describes the production of ethanol from hydrolysed whey permeate using *Saccharomyces cerevisiae* and a beta-galactosidase. In this study the authors obtained an ethanol yield of 0.49 using 10% dry solids in an SSF process. Because of a high beta-galactosidase concentration conversion of 90% of the lactose was completed in less than one hour.

In SSF hydrolysis/saccharification of lactose is carried out simultaneous with the fermentation and the lactase needs to have sufficient at the pH where the SSF is carried out, typically at a pH between 4.0 and 5.0.

It is the purpose of the present invention to improve ethanol yield of the above *S. cerevisiae* based simultaneous saccharification and fermentation process.

SUMMARY OF THE INVENTION

The invention provides an improved SSF process for producing ethanol from lactose containing substrates.

In a first aspect the present invention relates to a process for producing ethanol from lactose containing substrates, comprising simultaneously saccharifying the substrate to produce monosaccharide and fermenting the monosaccharide to produce ethanol at a pH from 3.5-5.5, using a fermenting organism, wherein saccharification is carried out in the presence of a lactase, and wherein the fermenting organism is a *Saccharomyces* sp., and the ratio between the incubation time required for obtaining at least 90% hydrolysis of the lactose present in the substrate ($t_1$) and the total fermentation time ($t_2$) is in the range of 0.1 to 1, and the *Saccharomyces* sp. is added in amounts that will result in an ethanol yield of at least 70% (w/w) of the theoretical ethanol yield from lactose by the end of fermentation.

In a second aspect the present invention relates a process for producing ethanol from starch-containing material comprising the steps of:
(a) liquefying starch-containing material in the presence of an alpha-amylase; and
(b) saccharifying the liquefied material obtained in step (a) and a lactose comprising substrate, using at least a glucoamylase and a lactase;
(c) fermenting using a yeast organism.

DETAILED DESCRIPTION OF THE INVENTION

Figure 1:
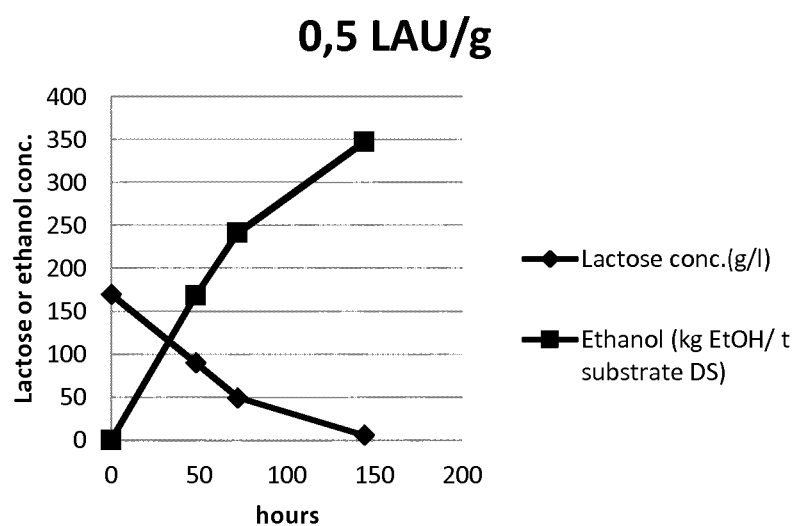
FIG. 1 shows ethanol yield and lactose hydrolysis as a function of fermentation time in SSF run at 32° C., pH 5.0 at 20% DS on a whey permeate substrate using *Bifidobacterium bifidum* lactase (SEQ ID NO: 2) at 0.5 LAU(A)/g DS.

The present invention relates to a process for saccharification and fermentation of a lactose containing substrate to produce ethanol.

More particularly the invention relates to a process for producing ethanol from lactose containing substrates, comprising simultaneously saccharifying the substrate to produce monosaccharide and fermenting the monosaccharide to produce ethanol at a pH from 3.5-5.5, using a fermenting organism, wherein saccharification is obtained by the presence of a lactase, and wherein the fermenting organism is a *Saccharomyces* sp., and the ratio between the incubation time required for obtaining at least 90% hydrolysis of the lactose present in the substrate ($t_1$) and the total fermentation time ($t_2$) is in the range of 0.1 to 1, and the *Saccharomyces* sp. is added in amounts that will result in an ethanol yield of at least 70% (w/w) of the theoretical ethanol yield from lactose by the end of fermentation.

According to the invention saccharification is obtained in the presence of a lactase (EC 3.2.1.23 and/or EC 3.2.1.108) and the ethanol yield of at least 70% w/w of the theoretical ethanol yield from lactose (53.8%) can be obtained by adjusting the enzyme dosage and fermentation time to arrive at a suitable $t_1/t_2$ ratio.

The reaction time necessary for obtaining at least 90% conversion/hydrolysis of the lactose is defined as $t_1$ and will depend on reaction conditions such as temperature, and pH and on the specific lactase enzyme and enzyme dosage.

In the context of the present invention lactose containing substrates comprise cheese whey, whey, whey permeate, acid whey, permeate mother liquor, and milk. Preferably the substrate is whey permeate or acid whey (e.g., a byproduct of Greek yoghurt).

Lactase Enzymes

A lactase in the context of the present invention is any glycoside hydrolase having the ability to hydrolyse the disaccharide lactose into constituent galactose and glucose monomers. The group of lactases comprises but is not limited to enzymes assigned to subclass EC 3.2.1.23. Enzymes assigned to EC 3.2.1.108, may also be lactases in the context of the present invention. A lactase in the context of the invention may have other activities than the lactose hydrolysing activity, such as for example a transgalactosylating activity. In the context of the invention, the lactose hydrolysing activity of the lactase may be referred to as its lactase activity or its beta-galactosidase activity.

Lactase activity according to the present invention may be determined according to the LAU(A) assay described in the examples herein. 1 lactase unit (1 LAU(A)) is the amount of enzyme which releases 1 μmol glucose per minute in M-buffer at pH 6.5 and 37° C. with a lactose concentration of 4.75% w/v.

Enzymes having lactase activity to be used in a method of the present invention may be of animal, of plant or of microbial origin. Preferred enzymes are obtained from microbial sources, in particular from a filamentous fungus or yeast, or from a bacterium. In particular the lactase enzyme used according to the invention may have optimum activity at a pH range between 3 and 7, preferably from pH 3.5 to 6.0, more preferably pH 4.0 to 5.5, such as around pH 5. The choice of lactase enzyme may depend on the pH of the lactose containing substrate.

The enzyme may, e.g., be derived from a strain of *Agaricus*, e.g. *A. bisporus*; *Ascovaginospora*; *Aspergillus*, e.g. *A. niger, A. awamori, A. foetidus, A. japonicus, A. oryzae*; *Candida*; *Chaetomium*; *Chaetotomastia*; *Dictyostelium*, e.g. *D. discoideum*; *Kluveromyces*, e.g. *K. fragilis, K. lactis*; *Mucor*, e.g. *M. javanicus, M. mucedo, M. subtilissimus*; *Neurospora*, e.g. *N. crassa*; *Rhizomucor*, e.g. *R. pusillus*; *Rhizopus*, e.g. *R. arrhizus, R. japonicus, R. stolonifer*; *Sclerotinia*, e.g. *S. libertiana*; *Torula*; *Torulopsis*; *Trichophyton*, e.g. *T. rubrum*; *Whetzelinia*, e.g. *W. sclerotiorum*; *Bacillus*, e.g. *B. coagulans, B. circulans, B. megaterium, B. novalis, B. subtilis, B. pumilus, B. stearothermophilus, B. thuringiensis*; *Bifidobacterium*, e.g. *B. Longum, B. bifidum, B. animalis*; *Chryseobacterium*; *Citrobacter*, e.g. *C. freundii*; *Clostridium*, e.g. *C. perfringens*; *Diplodia*, e.g. *D. gossypina*; *Enterobacter*, e.g. *E. Aerogenes, E. cloacae Edwardsiella, E. tarda*; *Erwinia*, e.g. *E. herbicola*; *Escherichia*, e.g. *E. coli*; *Klebsiella*, e.g. *K. pneumoniae*; *Miriococcum*; *Myrotheslum*; *Mucor*; *Neurospora*, e.g. *N. crassa*; *Proteus*, e.g. *P. vulgaris*; *Providencia*, e.g. *P. stuartii*; *Pycnoporus*, e.g. *Pycnoporus cinnabarinus, Pycnoporus sanguineus*; *Ruminococcus*, e.g. *R. torques*; *Salmonella*, e.g. *S. typhimurium*; *Serratia*, e.g. *S. liquefasciens, S. marcescens*; *Shigella*, e.g. *S. flexneri*; *Streptomyces*, e.g. *S. antibioticus, S. castaneoglobisporus, S. violeceoruber*; *Trametes*; *Trichoderma*, e.g. *T. reesei, T. viride*; *Yersinia*, e.g. *Y. enterocolitica*.

In a particular embodiment, the lactase enzyme is from *Aspergillus oryzae*.

In a preferred embodiment, the lactase enzyme is a lactase from a bacterium, e.g. from the family Bifidobacteriaceae, such as from the genus *Bifidobacterium*, such as from a strain of *B. bifidum, B. animalis* or *B. longum*. In a more preferred embodiment, the enzyme is a lactase from *Bifidobacterium bifidum*.

In a preferred embodiment, an enzyme having lactase activity to be used in a method of the present invention comprises or consists of the mature polypeptide of SEQ ID NO: 2.

In another preferred embodiment the lactase is selected from the mature polypeptide of SEQ ID NO: 2, or a lactase having at least 75%, at least 80%, at least 85%, at least 90%, at least 95%, at least 96%, at least 97%, at least 98%, at least 99% or 100% sequence identity to the mature polypeptide of SEQ ID NO: 2.

In a particular embodiment the mature polypeptide is amino acids 28 to 1331 of SEQ ID NO: 2.

In another preferred embodiment the lactase enzyme is obtained from *Aspergillus oryzae*, in particular the lactase is selected from Lactase F (available from Amano) or Tolerase™ L (available from DSM).

Lactase Enzyme Activity

In the context of the present application, 1 lactase unit (1 LAU(A)) is the amount of enzyme which releases 1 micromole glucose per minute in M-buffer at pH 6.5 and 37° C. with a lactose concentration of 4.75% w/v. M-buffer is prepared by dissolving 3.98 g $C_6H_5Na_3O_7$-$2H_2O$, 8.31 g citric acid, 0.9 g $K_2SO_4$, 2.6 g $K_2HPO_4$, 7.35 g $KH_2PO_4$, 5.45 g KOH, 4.15 g $MgCl_2$-$6H_2O$, 3.75 g $CaCl_2$-$2H_2O$ and 1.4 g $NaHCO_3$ in 4 liter water, adding 12.5 ml 4N NaOH, adjusting to pH 6.5 using HCl, and adding water up to a total volume of 5 liter.

The activity in LAU(A) of a specific lactase may be determined by direct measurement of glucose released from lactose under the conditions described above. The skilled person will know how to determine such activity. In particular, the activity may be determined by using the lactase activity assay described in Example 1 of the present application. Here, the activity is obtained by comparing to a standard curve run with a lactase of known activity, and the activity of the unknown sample calculated from this. The lactase of known activity may, e.g., be LACTOZYM PURE™ obtained from Novozymes A/S, Denmark, and available in different declared activities, e.g., Lactozym Pure 2600 L with a declared activity of 2600 LAU(A)/g.

However, the optimal lactase dosage applied depends on the desired total fermentation time ($t_2$). The reaction time necessary for obtaining at least 90% conversion/hydrolysis of the lactose is defined herein as $t_1$ and will depend on reaction conditions such as temperature, and pH and on the specific lactase enzyme and dosage. In order to obtain a desired ethanol yield of at least 70% w/w of the theoretical ethanol yield from lactose at the end of fermentation, $t_1$ and $t_2$ should according to the invention be adjusted to give $t_1/t_2$ in the range of 0.1 to 1.0, particularly 0.2 to 1.0, more particularly 0.3 to 1.0, more particularly 0.35 to 0.95.

As described above the process according to the invention relates to a process for producing ethanol from lactose containing substrates, comprising simultaneously saccharifying the substrate to produce monosaccharide and fermenting the monosaccharide to produce ethanol at a pH from 3.5-5.5, using a fermenting organism, wherein saccharification is carried out in the presence of a lactase, and wherein the fermenting organism is a *Saccharomyces* sp., and the ratio between the incubation time required for obtaining at least 90% hydrolysis of the lactose present in the substrate ($t_1$) and the total fermentation time ($t_2$) is in the range of 0.1 to 1, and the *Saccharomyces* sp. is added in amounts that will result in an ethanol yield of at least 70% w/w of the theoretical ethanol yield from lactose by the end of fermentation.

Optimal conditions will depend on both the hydrolysis time ($t_1$) and the total fermentation time ($t_2$). Short total fermentation times will thus also require short hydrolysis time. In order to achieve optimal fermentation conditions the ratio $t_1/t_2$ should be between 0.1 to 1, more particular 0.2 to 1, particularly 0.3 to 1, and more particular 0.35 to 0.95.

As industrial fermentation times are in the range of 10 to 200 hours the lactase activity should be adjusted in order to provide 90% hydrolysis within this time frame, so that $t_1/t_2$ is in the range described above.

In one embodiment the lactase activity is adjusted to provide at least 90% hydrolysis of the lactose substrate in 5 to 150 hours, particularly 10 to 130 hours, particularly 30 to 120 hours, more particularly in 40 to 100 hours, more particularly in 50 to 75 hours.

Accordingly in one embodiment fermentation time, $t_2$, is in the range from 10-200 hours, particularly 20-150 hours, more particularly 30-130 hours, more particularly 40-120 hours, even more particularly 50-100 hours.

In the examples this has been illustrated by using a specific lactase enzyme from *Bifidobacterium bifidum*, disclosed herein as the mature polypeptide of SEQ ID NO: 2. Moreover, the yeast pitch was selected to about $30 \times 10^6$, fermentation was performed at pH 5.0 and 32° C., and the fermentation time ($t_2$) was 150 hours.

It is a particular feature of the invention that the lactase units are adjusted so that the galactose, released from the lactose comprised in the substrate, is made available to the fermenting yeast organism in optimal amounts. It has surprisingly been found that in the case of lactose containing substrates having high dry solids (DS) content, in the present case 12% DS or more, the lactase activity during the fermentation phase has to be carefully controlled in order to reach the optimal ethanol yields by the end of the fermentation. As shown herein a pre-saccharification of the substrate resulting in complete hydrolysis of the lactose to glucose and galactose does not result in sufficiently high ethanol yields after fermentation. Surprisingly the yeast fermenting organism is only capable of utilizing the glucose but not galactose. Similarly, the galactose cannot be generated too fast, which is the case when the lactase activity is present in amounts of more than 2.0 LAU(A)/g DS using a lactase of SEQ ID NO: 2, at the specified pH, temperature, yeast pitch and fermentation time. It has also been found that galactose can be generated too slowly, which is the case when the lactase activity is present in amounts of less than 0.25 LAU(A)/g DS. The specific values of LAU(A)/g DS may vary depending on the specific lactase applied in the process according to the invention. What seems to be important is controlling the lactase activity in such a way that galactose is provided in optimal amounts.

According to the invention the lactase activity is in the range from 0.05 to 10.0 LAU(A)/g DS when e.g., a lactase from *Bifidobacterium*, in particular *Bifidobacterium bifidum*, is used. More particularly the lactase activity is in the range from 0.1 to 5.0 LAU(A)/g DS, particularly 0.25 to 3.0 LAU(A)/g DS, particularly 0.5 to 2 LAU(A)/g DS, and even more particularly in the range from 0.7 to 1.2 LAU(A)/g DS.

In a further embodiment of the process according to the invention it has been found that it is possible to reduce $t_1$, by increasing the LAU(A)/g DS, however this is only possible if the yeast fermenting organism has been preconditioned to grow in the presence of galactose. According to the invention this preconditioning is termed propagation and means that the yeast fermenting organism, in particular a *Saccharomyces* sp., is cultured in medium comprising galactose prior to the saccharification and fermentation step. Thus in this embodiment of the invention, the *Saccharomyces* sp. is propagated in a solution comprising galactose. In a particular embodiment the solution comprises 1% to 20% galactose, preferably 2% to 15% galactose, more preferably 5% to 10% galactose.

Propagation is at at least 6 hours, particularly at least 12 hours, more particularly at least 24 hours. In a further embodiment propagation is from 6-48 hours, particularly 12-24 hours.

An alternative to propagation would be recycling of the yeast fermenting organism. Thus after fermentation the fermenting organism may be separated from the fermented slurry and recycled.

The process according to the invention comprises hydrolysis (saccharification) and fermentation performed simultaneously (SSF).

When a propagation step is used, lactase activity present during the SSF can be increased and shorter fermentation times are then possible in order to obtain the same ethanol yield. Thus for $t_1/t_2$ it still applies that $t_1/t_2$ is in the range from 0.2 to 1, particularly 0.3 to 1, and more particular 0.35 to 0.95. Accordingly in one embodiment the lactase activity is adjusted to provide at least 90% hydrolysis of the lactose substrate in 5 to 100 hours, particularly 10 to 90 hours, particularly 20 to 80 hours, more particularly in 30 to 70 hours. Fermentation times can then also be shortened and thus in a further embodiment the fermentation time is in the range from 10-100 hours, particularly 20-90 hours, more particularly 40-80 hours, more particularly 50-75 hours, even more particularly 60-70 hours.

In one embodiment the lactase activity is in the range from 0.05 to 10.0 LAU(A)/g DS more particularly from 0.1 to 5.0 LAU(A)/g DS, particularly 0.5 to 3.0 LAU(A)/g DS, particularly 1.0 to 2.0 LAU(A)/g DS. The skilled person will know that the specific lactase units needed may depend on the choice of lactase enzyme. In particular the specific ranges disclosed herein have been determined based on the lactase disclosed herein as SEQ ID NO: 2. In this respect also the choice of lactose containing substrate can affect the exact range suitable according to the invention. The substrate pH may e.g., not correspond to the optimal working range for the lactase enzyme in which case more enzyme activity (e.g., a higher LAU(A)/g DS) has to be added. Thus in a further embodiment the lactase activity is in the range from 2-5 LAU(A)/gDS, more particularly from 3-5 LAU(A)/gDS, even more particularly from 4-5 LAU(A)/gDS.

Dry Solids Content (DS)

According to the invention the DS should preferably be at least 12%, such as least 13%, more particularly at least 14%, more particularly at least 15%, and even more particularly at least 20%. In one embodiment the DS is in the range from 12-40%, particularly from 15-30%, more particularly from 20-25%.

Fermenting Organism

In one embodiment the fermenting organism, the *Saccharomyces* sp., is added to the fermentation medium so that the viable count per mL of fermentation medium (yeast pitch) is in the range from $10^5$ to $10^{12}$, preferably from $10^6$ to $10^8$, such as around $10^7$, especially about $30 \times 10^6$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

Commercially available yeast include LNF SA-1, LNF BG-1, LNF PE-2,and LNF CAT-1 (available from LNF Brazil), RED STAR™ and ETHANOL RED™ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

In a further embodiment it is contemplated that the fermenting yeast is expressing the lactase in suitable amounts in order to provide a $t_1/t_2$ ratio in the range discussed herein. The skilled person will know how to regulate gene expression in yeast.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For ethanol production using yeast, the fermentation is carried out at a temperature between 20 to 40° C., preferably 28 to 36° C., in particular around 32° C. In an embodiment the pH is from pH 3 to 6, particularly pH from 3.5 to 5.5, preferably around pH 5.

Especially contemplated is simultaneous hydrolysis/saccharification and fermentation (referred to as "SSF") where there is no separate holding stage for the hydrolysis/saccharification, meaning that the hydrolysing enzyme(s), and the fermenting organism(s), are added together. When fermentation is performed simultaneous with saccharification (i.e., SSF) the temperature is preferably between 20 to 40° C., preferably 28 to 36° C., in particular around 32° C. when the fermentation organism is a strain of *Saccharomyces cerevisiae* and the desired fermentation product is ethanol.

In a particular embodiment the fermentation time ($t_2$) is at least 10 hours, more particularly at least 20 hours, more particularly at least 30 hours, more particularly at least 40 hours, more particularly at least 50 hours, more particularly at least 60 hours, more particularly at least 70 hours, more particularly at least 80 hours, more particularly at least 90 hours, more particularly at least 100 hours, more particularly at least 110 hours, more particularly at least 120 hours, more particularly at least 130 hours, more particularly at least 140 hours, more particularly at least 150 hours.

The total fermentation time is defined as $t_2$. In the case of continuous or fed-batch fermentations $t_2$ is defined as the mean residence time of the yeast in the fermenter.

Conventional Starch Processing

Native starch consists of microscopic granules, which are insoluble in water at room temperature. When an aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling are well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally liquefaction and liquefaction conditions are well known in the art.

Saccharification may be carried out using conditions well known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF).

The above described conventional starch ethanol process may in one embodiment be combined with the process according to the present invention. In this particular embodiment the present invention relates to a process for producing ethanol from starch-containing material comprising the steps of:
(a) liquefying starch-containing material in the presence of an alpha-amylase; and
(b) saccharifying the liquefied material obtained in step (a) and a lactose comprising substrate, using at least a glucoamylase and a lactase;
(c) fermenting using a yeast organism.

In particular, saccharification and fermentation are performed simultaneously (referred to as "SSF"). The lactose comprising substrate is in a particular embodiment whey permeate, acid whey, or milk.

Usually the mash is cooled after the liquefaction step and in a preferred embodiment the lactose substrate and/or the lactase is added to the mash during or after cooling or in a further embodiment the lactose substrate and/or the lactase is added prior to or during fermentation.

The present invention is further described by the following numbered paragraphs:

Paragraph [1]. A process for producing ethanol from lactose containing substrates, comprising simultaneously saccharifying the substrate to produce monosaccharide and fermenting the monosaccharide to produce ethanol at a pH from 3.5-5.5, using a fermenting organism, wherein saccharification is carried out in the presence of a lactase, and wherein the fermenting organism is a *Saccharomyces* sp., and the ratio between the incubation time required for obtaining at least 90% hydrolysis of the lactose present in the substrate ($t_1$) and the total fermentation time ($t_2$) is in the range of 0.1 to 1, and the *Saccharomyces* sp. is added in amounts that will result in an ethanol yield of at least 70% w/w of the theoretical ethanol yield from lactose by the end of fermentation.

Paragraph [2]. The process according to paragraph 1, wherein $t_1/t_2$ is in the range from 0.2 to 1, particularly 0.3 to 1, and more particular 0.35 to 0.95.

Paragraph [3]. The process according to paragraph 1-2, wherein the lactase activity is adjusted to provide at least 90% hydrolysis of the lactose substrate in 5 to 150 hours, particularly 10 to 130 hours, particularly 30 to 120 hours, more particularly in 40 to 100 hours, more particularly in 50 to 75 hours.

Paragraph [4]. The process according to any of the paragraphs 1-3, wherein the fermentation time is in the range from 10-200 hours, particularly 20-150 hours, more particularly 30-130 hours, more particularly 40-120 hours, even more particularly 50-100 hours.

Paragraph [5]. The process according to paragraph 1, wherein the lactase activity is in the range from 0.05 to 10.0 LAU(A)/g DS more particularly from 0.1 to 5.0 LAU(A)/g DS, particularly 0.25 to 3.0 LAU(A)/g DS, particularly 0.5 to 2 LAU(A)/g DS, and even more particularly in the range from 0.7 to 1.2 LAU(A)/g DS.

Paragraph [6]. The process according to paragraph 1, wherein the *Saccharomyces* sp. fermenting organism is propagated in a solution comprising galactose.

Paragraph [7]. The process according to paragraph 6, wherein the solution comprises 1% to 20% galactose, preferably 2% to 15% galactose, 5% to 10% galactose.

Paragraph [8]. The process according to paragraphs 6-7, wherein preincubation is at least 6 hours, particularly at least 12 hours, more particularly at least 24 hours.

Paragraph [9]. The process according to paragraphs 6-8, wherein the lactase activity is adjusted to provide at least 90% hydrolysis of the lactose substrate in 5 to 100 hours, particularly 10 to 90 hours, particularly 20 to 80 hours, more particularly in 30 to 70 hours.

Paragraph [10]. The process according to any of the paragraphs 6-9, wherein the fermentation time is in the range from 10-100 hours, particularly 20-90 hours, more particularly 40-80 hours, more particularly 50-75 hours, even more particularly 60-70 hours.

Paragraph [11]. The process according to any paragraphs 6-10, wherein the lactase activity is in the range from 0.05 to 10.0 LAU(A)/g DS more particularly from 0.1 to 5.0 LAU(A)/g DS, particularly 0.5 to 3.0 LAU(A)/g DS, particularly 1.0 to 2.0 LAU(A)/g DS.

Paragraph [12]. The process according to any of paragraphs 1-11, wherein the *Saccharomyces* sp. is *Saccharomyces cerevisiae*.

Paragraph [13]. The process according to any of the preceding paragraphs, wherein the Dry solid content, DS, is at least 12%, more particularly at least 13%, more particularly at least 14%, more particularly at least 15%, even more particularly at least 20%.

Paragraph [14]. The process according to any of the preceding paragraphs, wherein the lactose containing substrate is whey permeate, acid whey, or milk.

Paragraph [15]. The process according to any of the preceding paragraphs, wherein the lactase enzyme is obtained from a strain of *Bifidobacterium*, or from *Aspergillus*.

Paragraph [16]. The process according to paragraph 15, wherein the lactase enzyme is obtained from *Bifidobacterium bifidum*, or *Aspergillus oryzae*.

Paragraph [17]. The process according to any of the paragraphs 1-16, wherein the lactase is selected from the mature polypeptide of SEQ ID NO: 2, or a lactase having at least 90%, at least 95%, at least 96%, at least 97%, at least 98%, at least 99% or 100% sequence identity to the mature polypeptide of SEQ ID NO: 2.

Paragraph [18]. The process according to paragraph 17, wherein the mature polypeptide is amino acids 28 to 1331 of SEQ ID NO: 2.

Paragraph [19]. The process according to any of the paragraphs 1-18, wherein the lactase enzyme activity is provided by the yeast fermenting organism, expressing and secreting the lactase enzyme in suitable amounts.

Paragraph [20]. The process according to any of the preceding paragraphs wherein the yeast pitch is $10^6$-$10^8$, such as around $10^7$ viable count/ml.

Paragraph [21]. A process for producing ethanol from starch-containing material comprising the steps of:
(a) liquefying starch-containing material in the presence of an alpha-amylase; and
(b) saccharifying the liquefied material obtained in step (a) and a lactose comprising substrate, using at least a glucoamylase and a lactase;
(c) fermenting using a yeast organism.

Paragraph [22]. The process according to paragraph 21, wherein saccharification and fermentation are performed simultaneously.

Paragraph [23]. The process according to any of paragraphs 21-22, wherein the lactose comprising substrate is whey permeate, acid whey, or milk.

Paragraph [24]. The process according to any of paragraphs 21-23, further comprising the steps of:
a) cooling the liquefied substrate (mash) after the liquefaction step; and
b) adding a lactose substrate and the lactase to the mash during or after cooling.

Paragraph [25]. The process according to paragraph 21, wherein the lactose substrate and the lactase is added prior to or during fermentation.

The present invention is further described by the following examples that should not be construed as limiting the scope of the invention.

EXAMPLE 1

Determination of Lactase Activity (LAU(A))

Principle:

Lactase hydrolyses lactose into glucose and galactose. Glucose is measured after a modified version of the common glucose oxidase/peroxidase assay (Werner, W. et al. (1970) Z. analyt. Chem. 252: 224.).

The amount of glucose formed is determined using the GOD-Perid method:

Glucose-oxidase (β-D-glucose: oxygen-1-oxido-reductase, EC 1.1.3.4.) oxidises β-D-glucose in the presence of oxygen to δ-glucono-lactone and hydrogen-peroxide. The generated hydrogen-peroxide oxidises ABTS-R (2,2-Azino-di-(3-ethylbenzthiazoline)-6-sulfonate) in the presence of peroxidase (POD). This generates a green-blue colour, which is measured photometrically at 675 nm.

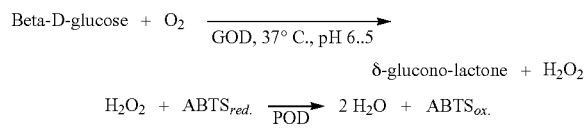

| Parameter | Reaction conditions |
|---|---|
| Temperature | 37° C. |
| pH | 6.5 |
| Substrate conc. | 50 g/L |
| Enzyme conc. | 0.0117-0.0333 LAU/mL |
| Reaction time | 30 min. |
| Wave length | 675 nm |

1 lactase unit (1 LAU(A)) is the amount of enzyme which releases 1 μmol glucose per minute in M-buffer at pH 6.5 and 37° C. with a lactose concentration of 4.75% w/v.

The detailed method is available from Novozymes NS on request.

EXAMPLE 2

Determination of Ethanol Yield as Function of Lactase Dosage in an SSF-Fermentation Assay The *Bifidobacterium bifidum* lactase disclosed in SEQ ID NO: 2 was tested in the process according to the invention. This lactase was used for all examples included.

Fermentation Assay:

Prepare 1 L 20% w/w whey permeate substrate (e.g. use Variolac 836 from Arla Foods).

Add urea (800 ppm) and adjust pH to pH 5.0

Add penicillin G (1 ppm) and yeast (Red Ethanol 30 $10^6$./ml)

Empty flask are weighed in advance 75 g substrate is transferred to 250 ml fermentation shaking flasks Add lactase according to schedule Flasks are weighed again, t=0

The fermentation flasks are placed in the shaking incubator at 32° C. (80 rpm)

Measure weight loss twice a day

HPLC measurement after 48, 72, and 144 hours (inactivate enzyme with HCl immediately after taking the sample)

Substrate:

Variolac® 836 from Arla Foods Ingredients

Chemical specifications:

| | |
|---|---|
| Protein (N × 6.38) as is | max. 5.0% |
| Lactose monohydrate | min. 83.0% |
| Ash | max. 10.0% |
| Moisture | Max. 3.0% |

The maltose content in Variolac 836 was determined to 87% by HPLC.

HPLC Analytic Method:

Two columns in series: BIO-RAD Aminex HPC-87H, cat no 128-014

Solvent: 0.005M $H_2SO_4$

Retention times (minutes) are:

Lactose=23.6; glucose=27.8; galactose=29.5

TABLE 1

The table shows ethanol yields obtained in SSF using different enzyme doses.

| Enzyme dose LAU(A)/g DS (SEQ ID NO: 2) | Time (SSF) Hours | Lactose g/l | Glucose g/l | Galactose g/l | Ethanol Kg/t substrate DS |
|---|---|---|---|---|---|
| 0.5 | 0 | 170 | 0 | 0 | 0 |
| 0.5 | 48 | 90.04 | 0.26 | 1.45 | 168.3 |

TABLE 1-continued

The table shows ethanol yields obtained in SSF using different enzyme doses.

| Enzyme dose LAU(A)/g DS (SEQ ID NO: 2) | Time (SSF) Hours | Lactose g/l | Glucose g/l | Galactose g/l | Ethanol Kg/t substrate DS |
|---|---|---|---|---|---|
| 0.5 | 72  | 49.37 | 0.29 | 2.03  | 241.6 |
| 0.5 | 144 | 5.87  | 0.40 | 2.16  | 347.3 |
| 1.0 | 0   | 170   | 0    | 0     | 0     |
| 1.0 | 48  | 31.13 | 0.42 | 13.77 | 248.9 |
| 1.0 | 72  | 5.92  | 0.63 | 21.00 | 292.7 |
| 1.0 | 144 | 1.04  | 0.84 | 17.24 | 320.6 |
| 2.0 | 0   | 170   | 0    | 0     | 0     |
| 2.0 | 48  | 7.11  | 7.11 | 57.35 | 208.9 |
| 2.0 | 72  | 4.17  | 4.17 | 55.96 | 213.3 |
| 2.0 | 144 | 2.41  | 2.41 | 45.43 | 226.2 |

Figure 2:
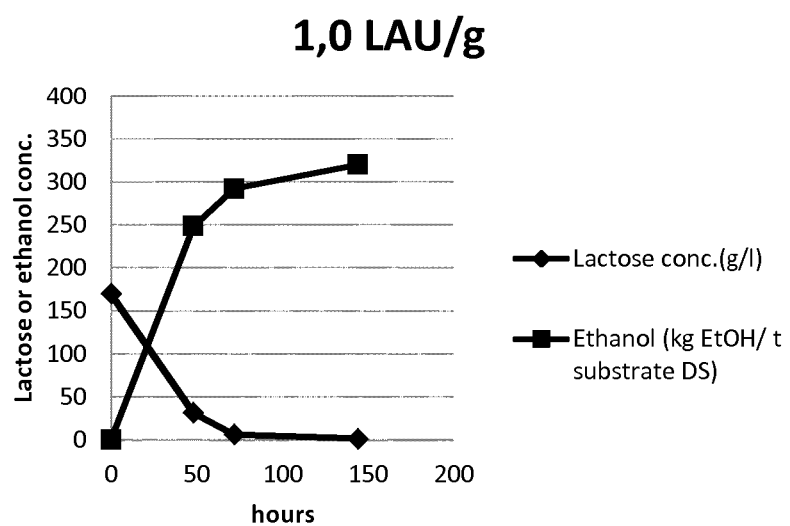
FIG. 2 shows ethanol yield and lactose hydrolysis as a function of fermentation time in SSF run at 32° C., pH 5.0 at 20% DS on a whey permeate substrate using *Bifidobacterium bifidum* lactase (SEQ ID NO: 2) at 1.0 LAU(A)/g DS.
Figure 3:
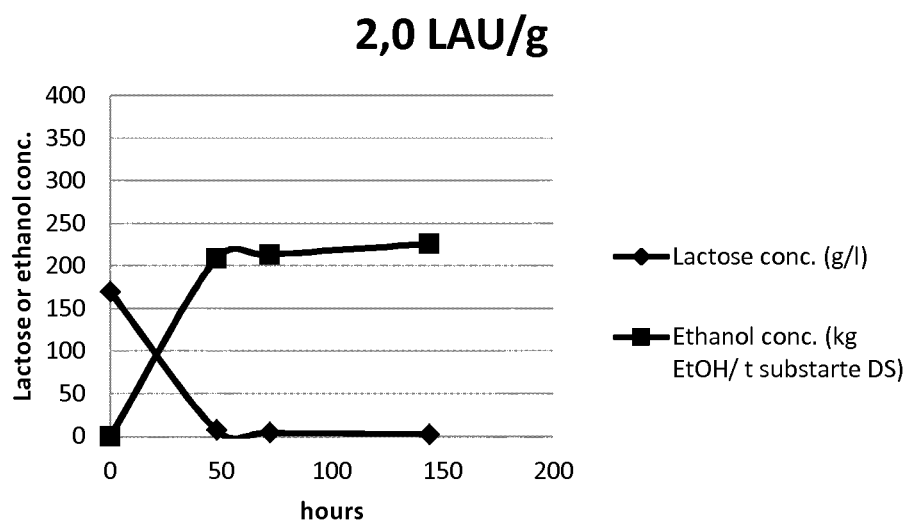
FIG. 3 shows ethanol yield and lactose hydrolysis as a function of fermentation time in SSF run at 32° C., pH 5.0 at 20% DS on a whey permeate substrate using *Bifidobacterium bifidum* lactase (SEQ ID NO: 2) at 2.0 LAU(A)/g DS.

The data from the table was plotted in FIGS. 1, 2 and 3. 100% conversion of the substrate corresponds to approximately 450 kg EtOH/t substrate DS.

The fermentation times resulting in a remaining lactose concentration of 10% (90% hydrolysis) can be read from the above graphs and are:

TABLE 2

| Enzyme dose | Time to 90% hydrolysis (hours) | $t_1/t_2$ |
|---|---|---|
| 0.5 LAU(A)/g DS | 130 | 0.9  |
| 1.0 LAU(A)/g DS | 60  | 0.42 |
| 2.0 LAU(A)/g DS | 45  | 0.31 |

Optimal performance was observed when the time to 90% hydrolysis was close to the total fermentation time and thus that the sugars were made available to the yeast simultaneously with the ethanol production.

EXAMPLE 3

Determination of Ethanol Yield as Function of Higher Lactase Dosages in an SSF-fermentation Assay The effect of increasing the enzyme dosage, *Bifidobacterium bifidum* lactase disclosed in SEQ ID NO: 2, was tested in a similar setup as described in example 2. Fermentation assay, substrate and HPLC were unchanged.

Figure 4:
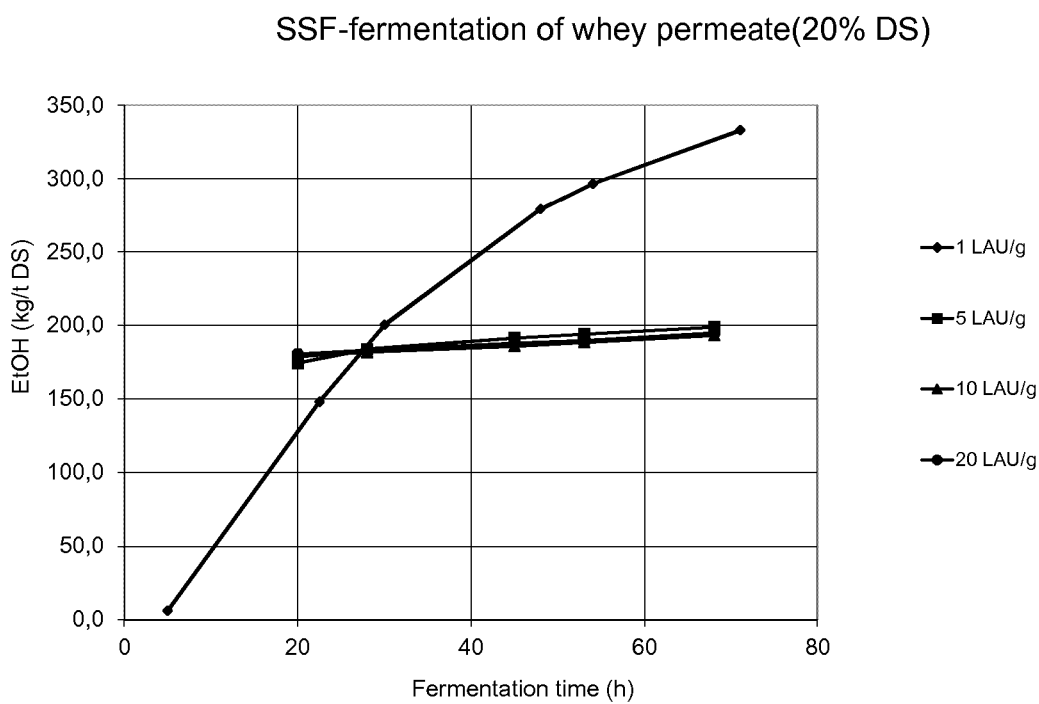
FIG. 4 shows ethanol yield as a function of fermentation time in SSF run at 32° C., pH 5.0 at 20% DS on a whey permeate substrate using *Bifidobacterium bifidum* lactase (SEQ ID NO: 2) at different lactase concentrations.

The results are shown in table 3 below and in FIG. 4.

TABLE 3

HPLC-data after 72 hours fermentation time:

| Enzyme dose | Lactose g/l | Glucose g/l | Galactose g/l | EtOH g/l | EtOH Kg/t substrate NB: based on weight loss |
|---|---|---|---|---|---|
| 1 LAU(A)/g  | 6.40 | 0.49 | 6.07  | 66.15 | 332.9 |
| 5 LAU(A)/g  | 4.11 | 0.57 | 73.74 | 39.66 | 198   |
| 5 LAU(A)/g  | 4.11 | 0.55 | 75.31 | 39.49 |       |
| 10 LAU(A)/g | 3.11 | 0.4  | 83.62 | 38.18 | 193   |
| 10 LAU(A)/g | 3.09 | 0.4  | 83.66 | 38.3  |       |
| 20 LAU(A)/g | 3.04 | 0.43 | 83.58 | 38.15 | 194   |
| 20 LAU(A)/g | 3    | 0.43 | 83.32 | 37.89 |       |

It is concluded from Example 3 that the yeast is not able to ferment galactose when the high LAU(A)-dosages are used in the SSF-fermentation even though the lactose is almost completely hydrolyzed.

EXAMPLE 4

Determination of Ethanol Yield in an SSF-fermentation Assay. Control Experiments with Galactose and Whey Permeate without Addition of Enzyme This example illustrates the effects of not adding any lactase enzyme to the whey permeate substrate or using a substrate containing only galactose (10% galactose).

Figure 5:
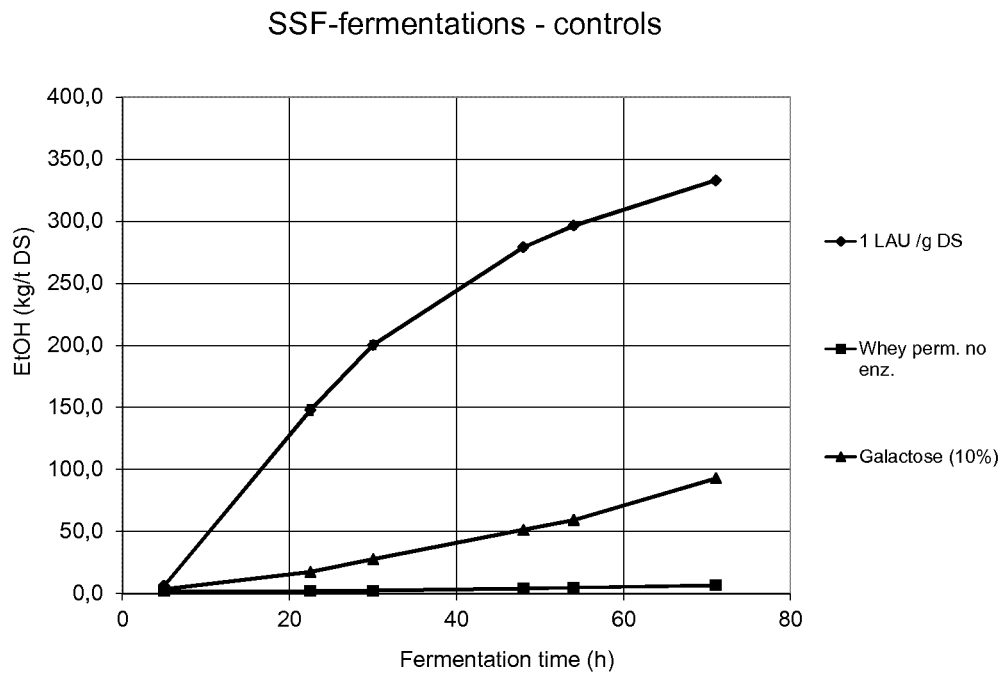
FIG. 5 shows ethanol yield and lactose hydrolysis as a function of fermentation time in SSF run at 32° C., pH 5.0 at 20% DS on a whey permeate substrate using *Bifidobacterium bifidum* lactase (SEQ ID NO: 2) at 1.0 LAU(A)/g DS. Included are controls having no lactase enzyme added and SSF performed on 10% galactose as substrate.
Figure 6:
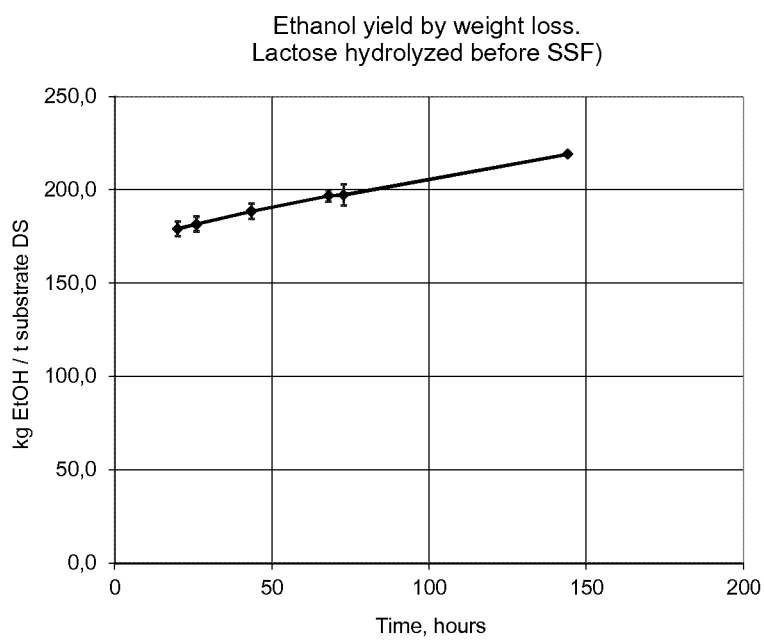
FIG. 6 shows kg EtOH/ton substrate DS as a function of fermentation time wherein EtOH yield was determined by weight loss.

Fermentation assay, Substrate, and HPLC-method as in Example 2 except that the substrate concentration was only 10% in the test with pure galactose. The result is shown in table 4 and in FIG. 5.

TABLE 4

HPLC-data for the test with 10% galactose:

| | Lactose g/l | Glucose g/l | Galactose g/l | EtOH g/l |
|---|---|---|---|---|
| Galactose (10% DS) | 3.56 | 0.07 | 72.49 | 9.86 |

The results show that without adding any lactase to the SSF process the *S. cerevisiae* fermenting organism is not capable of fermenting the lactose substrate, and that *S. cerevisiae* can only ferment pure galactose very slowly.

EXAMPLE 5

Determination of Ethanol Yield in an SSF-fermentation with Prehydrolyzed Whey Permeate Preparation of Substrate:

A 25% DS solution was made from whey permeate (Variolac 836) and DI water and incubated with Lactase added at a dosage of 20 LAU(A)/g DS. pH was adjusted to 5.0.

The solution is incubated at 32° C. over-night and then inactivated (boiled) for 10 minutes. After cooling the substrate is ready for fermentation. Samples were taken for HPLC analysis.

Fermentation assay and HPLC-method as in Example 2.

TABLE 5

HPLC-data:

| Time (SSF) Hours | Lactose g/l | Glucose g/l | Galactose g/l | Ethanol g/l |
|---|---|---|---|---|
| 0   | 3.2 | 110.3 | 112.8 | 0.9  |
| 48  | 2.9 | 0.2   | 94.8  | 46.1 |
| 72  | 5.8 | 0.2   | 91.0  | 49.5 |
| 144 | 2.7 | 0.4   | 83.4  | 53.3 |

It is concluded that yeast can ferment glucose, but only to a minor extent galactose when the lactose is hydrolyzed before fermentation.

EXAMPLE 6

Determination of Ethanol Yield as Function of Lactase Dosage in an SSF-fermentation Assay After Propagation in Galactose Fermentation assay, substrate, and HPLC-method as in Example 2 except that the yeast was propagated in galactose.

The procedure for yeast propagation was:

The yeast was taken out of the fridge and suspended in demineralized water. Galactose was added to a concentration of 10% w/w and agitated for 24 hours at room temperature before use.

Figure 7:
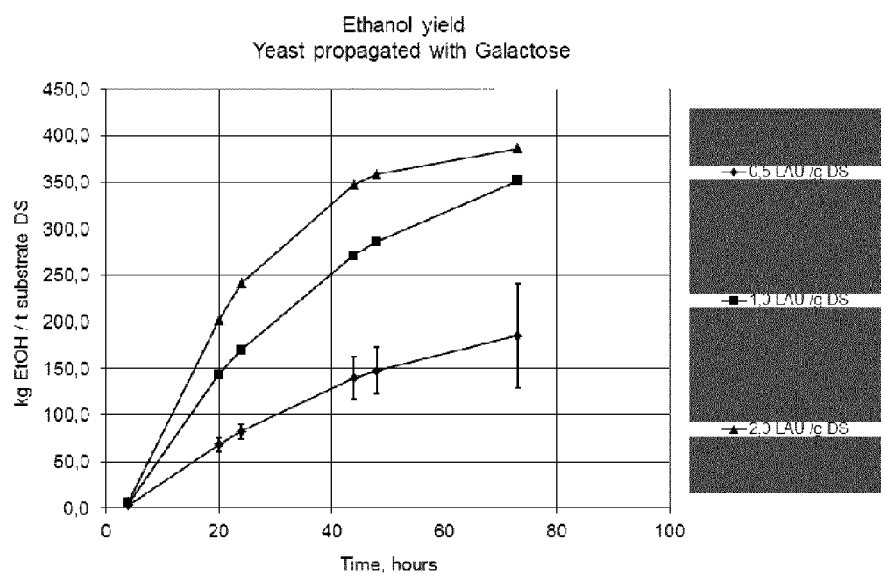
FIG. 7 shows ethanol yield (kg EtOH/ton substrate DS) as function of fermentation time at three different lactose concentrations.

Ethanol yield data is shown in table 6 below and in FIG. 7.

TABLE 6

HPLC data (after 72 hours):

| | Lactose g/l | Glucose g/l | Galactose g/l | EtOH g/l |
|---|---|---|---|---|
| 0.5 LAU(A)/g DS | 70.2 | 0.3 | 0.5 | 44.5 |
| 1.0 LAU(A)/g DS | 0.9 | 0.7 | 0.1 | 78.6 |
| 2.0 LAU(A)/g DS | 0.6 | 0.6 | 0.1 | 79.8 |

EXAMPLE 7

Determination of Ethanol Yield as Function of Lactase Dosage in an SSF-fermentation Assay After Propagation in Glucose+Galactose Fermentation assay, substrate, and HPLC-method as in Example 2 except that the yeast was propagated in mixture of 10% glucose and 10% galactose.

The procedure for yeast propagation was:

The yeast was taken out of the fridge and suspended in demineralized water. Glucose and galactose was added to a concentration of 10% w/w each and agitated for 24 hours before use.

Figure 8:
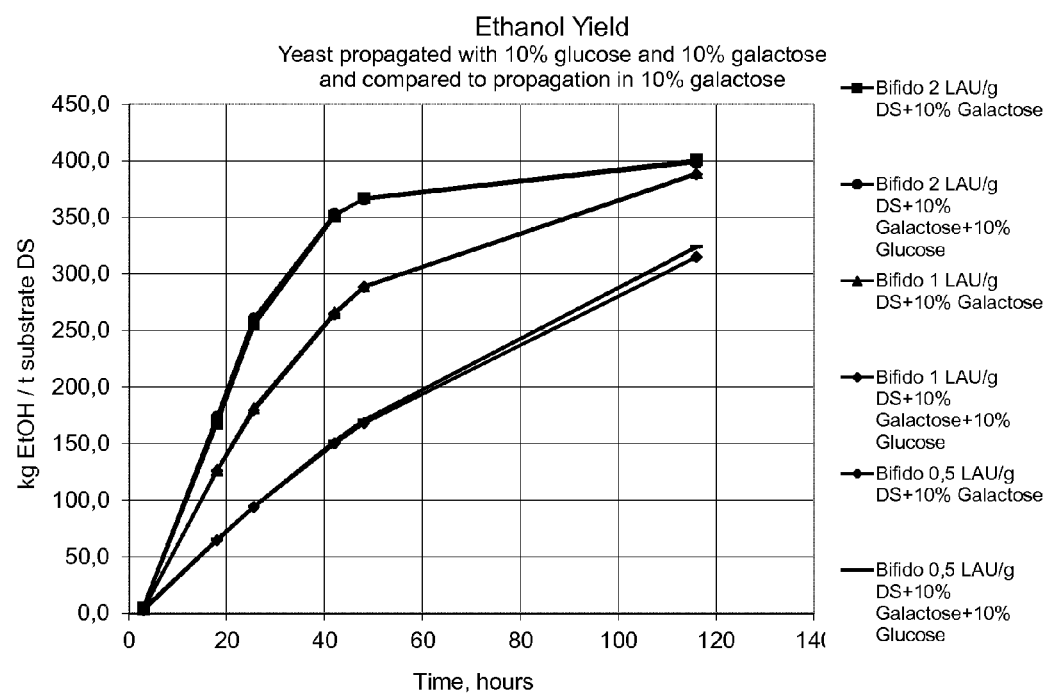
FIG. 8 shows ethanol yield (kg EtOH/ton substrate DS) as function of lactase dosage in an SSF-fermentation assay after propagation in glucose +galactose.

Ethanol yield data is shown in table 7 and in FIG. 8. The results obtained were identical when the same lactase concentration was used with or without glucose present. Therefore the resulting curves cannot be distinguished.

TABLE 7

HPLC data (after 116 hours):

| Sample | EtOH (g/l) |
|---|---|
| 0.5 LAU(A)/g DS; propagated in 10% galactose | 65.4 |
| 0.5 LAU(A)/g DS; propagated in 10% galactose + 10% glucose | 67.4 |
| 1 LAU(A)/g DS; propagated in 10% galactose | 79.7 |
| 1 LAU(A)/g DS; propagated in 10% galactose + 10% glucose | 80.0 |
| 2 LAU(A)/g DS; propagated in 10% galactose | 82.0 |

TABLE 7-continued

HPLC data (after 116 hours):

| Sample | EtOH (g/l) |
|---|---|
| 2 LAU(A)/g DS; propagated in 10% galactose + 10% glucose | 82.9 |

The propagation in 10% glucose and 10% galactose simulates propagation in a 20% lactose solution hydrolyzed with lactase. The result showed that presence of glucose did not have an effect.

EXAMPLE 8

Determination of Ethanol Yield with Recycling of the Yeast

Fermentation assay, substrate, and HPLC-method as in Example 2 except that the yeast was recycled from a previous fermentation.

The procedure for yeast recycle was:

The yeast from Example 7, the test with propagation in 10% galactose, was split in two equal parts after the fermentation and used as the recycled yeast in this experiment.

Figure 9:
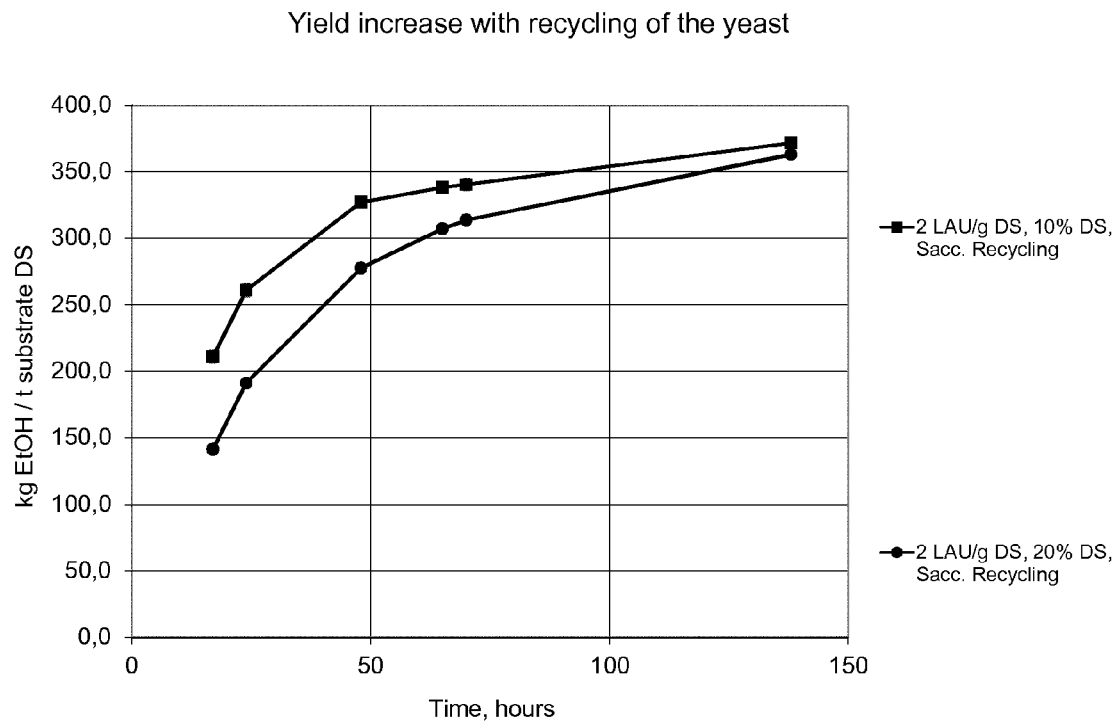
FIG. 9 shows ethanol yield (kg EtOH/ton substrate DS) as function of fermentation time at different % DS and using recycling of the yeast cells.

The result is shown in FIG. 9 in which the ethanol yield is plotted as a function of fermentation time. The end final ethanol yield was about the same level for both tested dry solid concentrations. Compared to data obtained by not using recycling (see example 2, table 1 and FIG. 3) the results show that higher ethanol yield can be reached by recycling the yeast compared to adding the lactose during the SSF step (0.5-1.0 LAU(A) was the optimal lactose concentration under the conditions in example 2).

Figure 10:
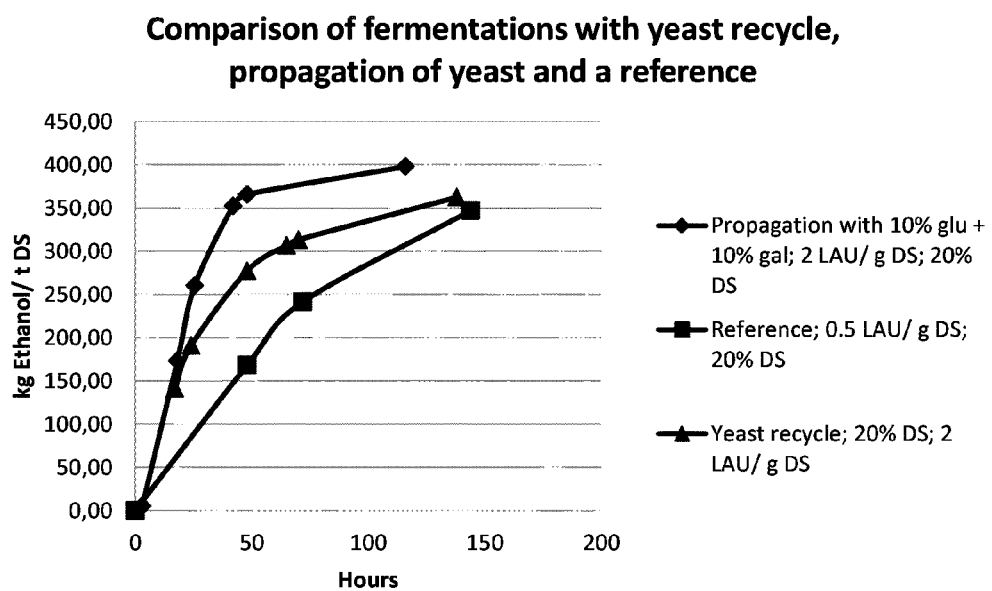
FIG. 10 shows a comparison of the obtained ethanol yield (kg EtOH/ton substrate DS) as function of fermentation time using i) propagation in 10% galactose, ii) no propagation, iii) recycling of the yeast.

Data in FIG. 10 illustrates the optimal ethanol yields obtainable using three different embodiments of the process according to the invention. Embodiment 1 is adding the lactase to the SSF step in the optimal dosage range (about 0.5 LAU(A)/g DS). Embodiment 2 includes recycling of the yeast and adding lactose in the optimal dosage range (about 2.0 LAU(A)/g DS). Embodiment 3 includes propagation of the yeast in 10% galactose and 10% glucose (simulating a 20% whey permeate substrate) prior to SSF and using the same lactose dosage as embodiment 2.

The data are from example 2, 7, and 8 and the results show that the highest possible ethanol yield was reached using embodiment 3 (propagation of the yeast) followed by embodiment 2 (recycling of the yeast).

The invention claimed is:

1. A process for producing ethanol from lactose containing substrates, comprising simultaneously saccharifying the substrate to produce monosaccharide and fermenting the monosaccharide to produce ethanol at a pH from 3.5-5.5, using a fermenting organism, wherein saccharification is carried out in the presence of a lactase, wherein the lactase is amino acids 28 to 1331 of the polypeptide of SEQ ID NO: 2, or a lactase having at least 90% sequence identity to amino acids 28 to 1331 of SEQ ID NO: 2, and wherein the fermenting organism is a *Saccharomyces* sp., and the ratio between the incubation time required for obtaining at least 90% hydrolysis of the lactose present in the substrate ($t_1$) and the total fermentation time ($t_2$) is in the range of 0.1 to 1, and wherein the fermentation time is in the range from 20-150 hours and the lactase activity is added in a range from 0.1 to 5.0 LAU(A)/g Dry Solid Content (DS).

2. The process according to claim 1, wherein $t_1/t_2$ is in the range from 0.2 to 1.

3. The process according to claim 1, wherein the lactase activity is adjusted to provide at least 90% hydrolysis of the lactose substrate in 5 to 150 hours.

4. The process according to claim 1, wherein the fermentation time is in the range from 30-130 hours.

5. The process according to claim 1, wherein the lactase activity is in the range from 0.25 to 3.0 LAU(A)/g DS.

6. The process according to claim 1, wherein the *Saccharomyces* sp. fermenting organism is propagated in a solution comprising galactose.

7. The process according to claim 6, wherein the solution comprises 1% to 20% galactose.

8. The process according to claim 6, wherein the lactase activity is adjusted to provide at least 90% hydrolysis of the lactose substrate in 5 to 100 hours.

9. The process according to claim 6, wherein the fermentation time is in the range from 20-90 hours.

10. The process according to claim 6, wherein the lactase activity is in the range from 0.5 to 3.0 LAU(A)/g DS.

11. The process according to claim 1, wherein the *Saccharomyces* sp. is *Saccharomyces cerevisiae*.

12. The process according to claim 1, wherein the DS is at least 12%.

13. The process according to claim 1, wherein the lactose containing substrate is whey permeate, acid whey, or milk.

14. The process according to claim 1, wherein the lactase enzyme is obtained from a strain of *Bifidobacterium*, or from *Aspergillus*.

15. The process according to claim 14, wherein the lactase enzyme is obtained from *Bifidobacterium bifidum*, or *Aspergillus oryzae*.

16. The process according to claim 1, wherein the yeast pitch is $10^6$-$10^8$ viable count/ml.

17. The process according to claim 1, wherein the fermentation time is in the range from 40-120 hours.

18. The process according to claim 1, wherein the fermentation time is in the range from 50-100 hours.

19. The process according to claim 1, wherein the lactase activity is in the range from 0.5 to 2 LAU(A)/g DS.

20. The process according to claim 1, wherein the lactase activity is in the range from 0.7 to 1.2 LAU(A)/g DS.

21. The process according to claim 6, wherein the fermentation time is in the range from 40-80 hours.

22. The process according to claim 6, wherein the fermentation time is in the range from 50-75 hours.

23. The process according to claim 6, wherein the fermentation time is in the range from 60-70 hours.

24. The process according to claim 6, wherein the lactase activity is in the range from 1.0 to 2.0 LAU(A)/g DS.

* * * * *